(12) United States Patent
Ein-Gal (10) Patent No.: US 6,275,564 B1
(45) Date of Patent: Aug. 14, 2001

(54) POSITIONER FOR RADIATION TREATMENT

(76) Inventor: Moshe Ein-Gal, 30 Azar Street, Ramat Hasharon (IL), 47203

( * ) Notice: Subject to any disclaimer, the term of this patent is extended or adjusted under 35 U.S.C. 154(b) by 0 days.

(21) Appl. No.: 09/346,223

(22) Filed: Jul. 1, 1999

(30) Foreign Application Priority Data

Aug. 5, 1998 (IL) ........................................................ 125676

(51) Int. Cl.[7] ............................................................. A61N 5/10
(52) U.S. Cl. ................................................. 378/68; 378/65
(58) Field of Search ................................. 378/65, 64, 68, 378/69, 205, 206

(56) References Cited

U.S. PATENT DOCUMENTS 5,745,545 * 4/1998 Hughes ...................................... 378/65
6,134,294 * 10/2000 Gibbs ....................................... 378/65

* cited by examiner

Primary Examiner—David P. Porta
(74) Attorney, Agent, or Firm—Townsend and Townsend and Crew, LLP (57) ABSTRACT

A positioner useful in stereotactic radiation treatment of a patient by radiation from a radiation source from which a radiation beam is emitted along a beam axis, the positioner including a source adapter arm arranged to be attached to the radiation source such that the position of the source adapter arm is determined by the position of the radiation source, and a frame adapter arm pivotably attached to the source adapter arm about a pivot axis, the frame adapter arm defining a frame axis intersecting the pivot axis, the pivot axis and the frame axis being selected such that when the source adapter arm is attached to the radiation source, the pivot axis and the frame axis both intersect the beam axis.

19 Claims, 7 Drawing Sheets

POSITIONER FOR RADIATION TREATMENT

FIELD OF THE INVENTION

The present invention relates generally to positioning systems for stereotactic radiation treatment, and particularly to a positioner for use with a radiation source housing and patient support table, the positioner ensuring that a radiation beam passes through an isocenter regardless of the relative movement or sagging of the table and the source housing.

BACKGROUND OF THE INVENTION

It is imperative in stereotactic radiation treatment to ensure that radiation beam, such as a linear accelerator (LINAC) central beam of radiation, passes as close as possible to the ideal isocenter, i.e., the theoretical intersection of a rotational axis (azimuth axis) of a table which carries the target (patient) and a rotational axis (elevation or roll axis) of the LINAC gantry. In general, the target lies in the patient's head and a stereotactic frame is provided for holding the head fixed with respect to the floor or the treatment table. The purpose of fixing the stereotactic frame is to ensure that the radiation beam always passes substantially through the isocenter during radiation treatment. One way of fixing the stereotactic frame is by mounting it on the table. Another way is to fix the stereotactic frame with respect to the floor. In each case, means are provided for attempting to position the frame such that the target is substantially in the isocenter.

In practice, however, while the heavy gantry moves to various gantry angles, the LINAC head sags. Moreover, the rotary bearing of the LINAC and/or the table are not ideal and this affects concentricity, inter alia. Consequently, the central radiation beam does not intersect the ideal isocenter. Thus, in general, unpredictable deformations of the structures supporting the radiation source or the target, as well as errors in determining the positions of the source or the target lead to inaccuracies in delivering the radiation beam to the isocenter.

SUMMARY OF THE INVENTION

The present invention seeks to provide an improved positioner for use with a radiation source housing and patient support table. The positioner is attachable to a radiation system having two axes of rotation for stereotactic treatment. The two axes may be the turning axes of the LINAC and table, for example. The positioner has its own axes of rotation independent of the rotational axes of the radiation system. When the positioner is attached to the radiation system, the rotational axes of the positioner are placed close to, but not necessarily collinear with, the rotational axes of the system. The target is rigidly referenced to the positioner. Thus, the target is irradiated with a precision determined by the positioner and not the radiation system.

The positioner comprises two rigid arms, one for attachment to the source housing and the other attachable to a stereotactic frame. The two arms pivot about a common axis and define an isocenter that always remains aligned with a radiation beam emanating from the radiation source regardless of the relative movement or sagging of the table and the radiation source housing. The two arms thus move in precise relation with the azimuthal, elevational and/or roll movements of the gantry and/or table.

There is thus provided in accordance with a preferred embodiment of the present invention a positioner useful in stereotactic radiation treatment of a patient by radiation from a radiation source from which a radiation beam is emitted along a beam axis, the positioner including a source adapter arm arranged to be attached to the radiation source such that the position of the source adapter arm is determined by the position of the radiation source, and a frame adapter arm pivotably attached to the source adapter arm about a pivot axis, the frame adapter arm defining a frame axis intersecting the pivot axis, the pivot axis and the frame axis being selected such that when the source adapter arm is attached to the radiation source, the pivot axis and the frame axis both intersect the beam axis.

In accordance with a preferred embodiment of the present invention the pivot axis and the frame axis are selected such that when the source adapter arm is attached to the radiation source, the pivot axis and the frame axis both intersect the beam axis generally at the same location, and most preferably, substantially at the same location. Preferably the pivot axis and the frame axis are generally orthogonal.

Further in accordance with a preferred embodiment of the present invention the positioner also includes a source adapter arm positioning assembly which adjusts attachment of the source adapter arm to the radiation source.

Still further in accordance with a preferred embodiment of the present invention the positioner also includes a patient support frame pivotably mounted to the frame adapter arm.

Additionally in accordance with a preferred embodiment of the present invention the positioner also includes a frame adapter arm positioning assembly which adjusts mounting of the patient support frame to the frame adapter arm.

In accordance with a preferred embodiment of the present invention the positioner also includes a beam collimator mounted onto the source adapter arm for collimating the radiation beam.

There is also provided in accordance with a preferred embodiment of the present invention a stereotactic radiation treatment system for treatment of a patient by radiation, including a radiation source from which a radiation beam is emitted along a beam axis, and a positioner including a source adapter arm arranged to be attached to the radiation source such that the position of the source adapter arm is determined by the position of the radiation source, and a frame adapter arni pivotably attached to the source adapter arm about a pivot axis, the frame adapter arm defining a frame axis intersecting the pivot axis, the pivot axis and the frame axis being selected such that when the source adapter arm is attached to the radiation source, the pivot axis and the frame axis both intersect the beam axis.

Preferably the stereotactic radiation treatment system also includes a patient support frame with respect to which a patient can be rigidly mounted such that a target area of the patient is located at an intersection of the pivot axis, the frame axis and the beam axis.

In accordance with a preferred embodiment of the present invention the source adapter arm is suspended from the radiation source. Alternatively in accordance with another preferred embodiment of the present invention the source adapter arm is at least partially suspended from the radiation source.

Further in accordance with a preferred embodiment of the present invention the stereotactic radiation treatment system includes a support element for supporting at least one of the source adapter arm and the frame adapter arm.

There is also provided in accordance with a preferred embodiment of the present invention a positioner useful in stereotactic radiation treatment of a patient by radiation from a radiation source from which a radiation beam is emitted along a beam axis, the positioner including a source adapter arm arranged to be attached to the radiation source such that the position of the source adapter arm is determined by the position of the radiation source, and the position of the source adapter arm relative to the radiation source is independent of the position of the gantry arm relative to the radiation source, and a measurement assembly mounted on the source adapter arm for making measurements with respect to a measurement axis, the measurement axis initially substantially intersecting the beam axis, the measurement assembly measuring a misalignment of the measurement axis with the beam axis.

In accordance with a preferred embodiment of the present invention the positioner also includes a patient support frame which includes a frame axis about which a patient is rotatable, wherein the patient is rigidly mountable to the support frame such that a target of the patient is located at an intersection of the beam axis, the measurement axis and the frame axis.

Further in accordance with a preferred embodiment of the present invention the positioner also includes a target assembly which includes a bar slidingly attached to the patient support frame so that the bar is adjustable along any of three mutually perpendicular axes with respect to the frame, and wherein at least one marker extends from the bar, the marker being sensed by the measurement assembly and the marker being accurately positionable with respect to the beam axis, the measurement axis and the frame axis. Preferably the at least one marker always remains at a constant, known predetermined spatial distance from the target.

Still further in accordance with a preferred embodiment of the present invention the bar is adjusted with respect to the patient support frame so that at least one of the beam axis and the frame axis substantially passes through a reference point of the marker. Preferably there are two markers which are positioned so that they are substantially equidistant from the target.

In accordance with a preferred embodiment of the present invention the measurement assembly includes an optical measurement assembly.

Further in accordance with a preferred embodiment of the present invention the measurement assembly measures angular position changes of the at least one marker relative to at least one of the beam axis, the measurement axis and the frame axis.

Still further in accordance with a preferred embodiment of the present invention the measurement assembly measures linear position changes of the at least one marker relative to at least one of the beam axis, the measurement axis and the frame axis.

Additionally in accordance with a preferred embodiment of the present invention the source adapter arm is telescopic.

In accordance with a preferred embodiment of the present invention the measurement axis is offset generally parallel to a rotational axis of a gantry arm, thereby defining a new isocenter at an intersection of the measurement axis and the frame axis.

In accordance with a preferred embodiment of the present invention the measurement assembly includes a light source which emits a light beam which impinges on a coordinate board at an impingement point, the coordinate board having a fixed, known spatial relationship with an intersection of the beam axis and the measurement axis, and preferably the frame axis as well.

Further in accordance with a preferred embodiment of the present invention a pin protrudes from a surface of the coordinate board, the pin having a point with a fixed, known spatial relationship with an intersection of the beam axis and the measurement axis and preferably the frame axis as well.

BRIEF DESCRIPTION OF THE DRAWINGS

The present invention will be understood and appreciated more fully from the following detailed description, taken in conjunction with the drawings in which.

DETAILED DESCRIPTION OF A PREFERRED EMBODIMENT

Figure 1:
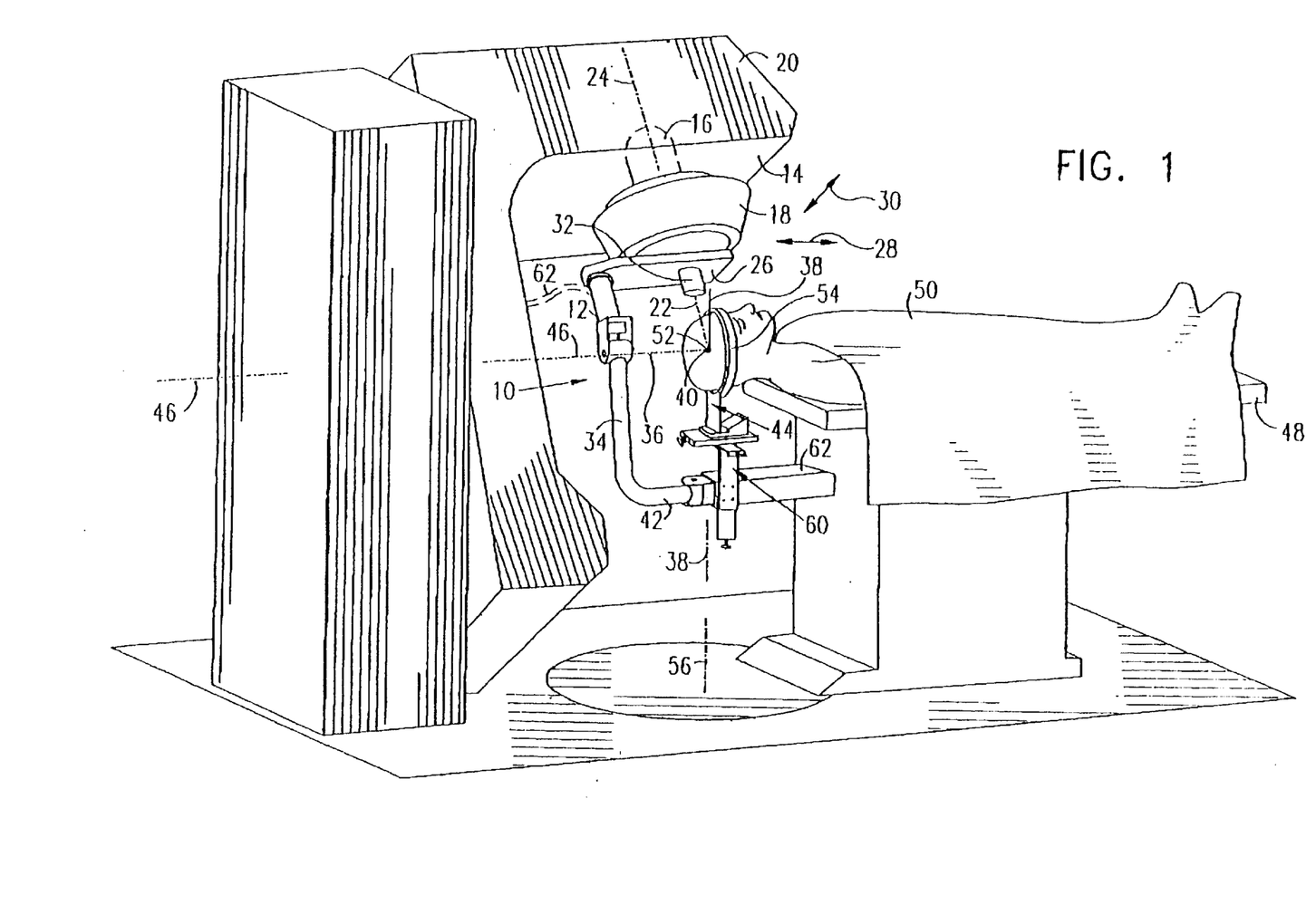
FIG. 1 is a simplified pictorial illustration of a positioner for stereotactic radiation treatment constructed and operative in accordance with a preferred embodiment of the present invention.

Reference is now made to FIG. 1 which illustrates a positioner 10 for stereotactic radiation treatment, constructed and operative in accordance with a preferred embodiment of the present invention.

Positioner 10 includes a source adapter arm 12 arranged to be attached to a housing 14 of a radiation source 16. For example, arm 12 may be suspended or at least partially suspended from a portion of a tray or turret 18 of a LINAC gantry 20. Radiation source 16 emits a radiation beam 22 along a beam axis 24. Preferably a source adapter arm positioning assembly 26 is provided for adjusting attachment of arm 12 to the radiation source 16. Assembly 26 may adjust the position of arm 12 relative to radiation source 16 along and/or about any of three mutually orthogonal axes, such as axes 28 and 30 (in a plane perpendicular to beam axis 24) and beam axis 24, for example. Assembly 26 may include any conventional step motor, actuator or the like, for adjusting the position of arm 12. A beam collimator 32 is preferably mounted onto arm 12 for collimating radiation beam 22. By virtue of the attachment of arm 12 to radiation source 16, the spatial position of arm 12 is determined by the position of radiation source 16.

A frame adapter arm 34 is pivotably attached to source adapter arm 12 about a pivot axis 36. Arm 34 defines a frame axis 38 intersecting pivot axis 36. Pivot axis 36 and frame axis 38 are selected such that when arm 12 is attached to radiation source 16, pivot axis 36 and frame axis 38 both intersect beam axis 24. Preferably pivot axis 36 and frame axis 38 both intersect beam axis 24 generally at the same location, and most preferably substantially at the same location, designated by reference numeral 40. Pivot axis 36 and frame axis 38 are preferably generally orthogonal.

Arm 34 includes a distal portion 42 which is preferably attached to a patient support frame 44 such that frame 44 is rotatable about frame axis 38. As seen in FIG. 1, frame axis 38 is preferably the azimuth axis and pivot axis 36 is preferably the roll axis.

Gantry 20, comprising therein radiation source 16, is rotatable about a gantry axis 46, as is well known in the art. Radiation source 16 generally rotates about gantry axis 46 synchronously with rotation of either one or both of arms 12 and 34 about pivot axis 36. Gantry axis 46 ideally generally coincides with pivot axis 36. However, it is a particular feature of the present invention that even if gantry axis 46 is misaligned with pivot axis 36, source adapter arm 12 always positions location 40 (located at the isocenter) in a desired orientation with respect to radiation source 16, i.e., radiation beam 22 substantially intersects location 40 no matter how gantry 20 has moved or sagged. Source adapter arm 12 succeeds in accurately positioning location 40 relative to radiation source 16 by virtue of arm 12 being stiff and rigidly suspended, or at least partially suspended, from housing 14.

Alternatively, in accordance with another preferred embodiment of the present invention, arms 12 and 34 can be configured or positioned such that pivot axis 36 is purposely misaligned with (i.e., offset from) gantry axis 46 so as to enable carrying out irradiation schemes which may not be possible with rotation about gantry axis 46 of LINAC gantry 20.

There is preferably provided a table 48 upon which a patient 50 may be supported. Patient 50 has a target 52 which is to be irradiated by radiation beam 22. In the illustrated example, the head of patient 50 is affixed to a head ring 54 of frame 44 such that location 40 lies in target 52. Table 48 is rotatable about a table axis 56, as is well known in the art. Table 48 generally rotates about table axis 56 synchronously with rotation of either one or both of arms 12 and 34 about frame axis 38. Table axis 56 ideally generally coincides with frame axis 38. In a similar fashion as stated hereinabove, it is a particular feature of the present invention that even if table axis 56 is misaligned with frame axis 38, source adapter arm 12 always positions isocenter 40 in a desired orientation with respect to radiation source 16 and frame adapter arm 34 always positions isocenter 40 in a desired orientation with respect to patient support frame 44, i.e., radiation beam 22 substantially intersects location 40 and target 52 no matter how gantry 20 or table 48 has moved or sagged. Radiation source 16 thus "drags" the target of the patient with it no matter where it goes or how it sags, and accurate irradiation of the target is ensured.

A frame adapter arm positioning assembly 60, such as an X-Y-Z positioner, is preferably pivotably mounted to frame adapter arm 34 and attached to patient support frame 44. Assembly 60 adjusts mounting of patient support frame 44 to arm 34. Assembly 60 moves patient support frame 44 along three mutually orthogonal axes (typically corresponding to axes 36 and 38 and to beam axis 24), so that target 52 can be properly aligned with location 40.

Although arms 12 and 34 are preferably stiffly cantilevered from turret 18, if desired, a support element 62 may be optionally provided for supporting either one of arms 12 or 34 without hindering the free movement of the arms.

Figure 2:
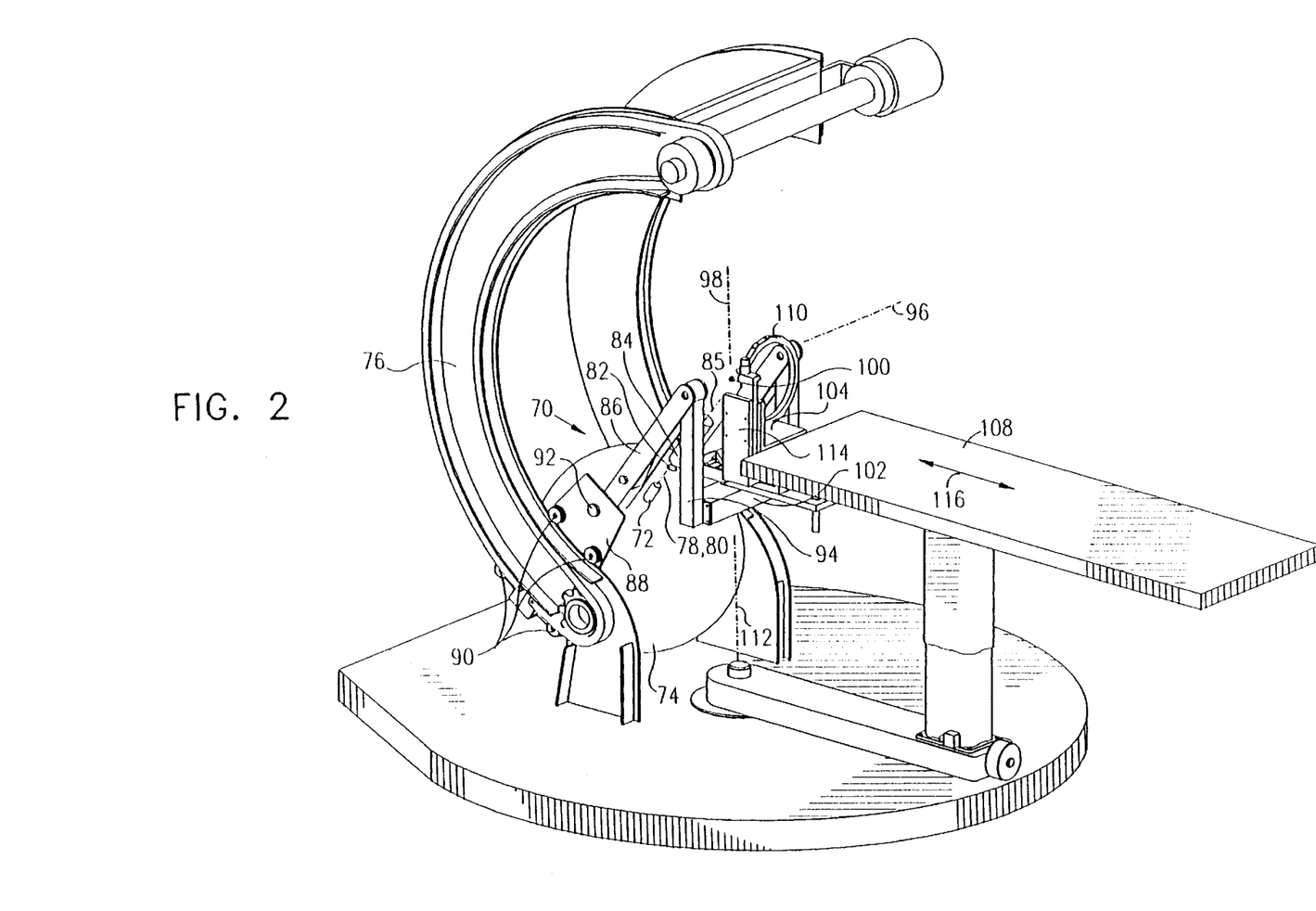
FIG. 2 is a simplified pictorial illustration of a positioner for stereotactic radiation treatment constructed and operative in accordance with another preferred embodiment of the present invention.

Reference is now made to FIG. 2 which illustrates a positioner 70 for stereotactic radiation treatment, constructed and operative in accordance with another preferred embodiment of the present invention.

Positioner 70 is particularly useful with a radiation system having a radiation source 72 housed in a radiation shield 74, typically generally spherical in shape, as seen in FIG. 2. Radiation shield 74 together with radiation source 72 are arranged to slide along a generally arcuate track 76. Track 76 may be circular, elliptic, parabolic or any other curvilinear shape. Radiation source 72 emits a radiation beam 78 along a radiation axis 80. Radiation beam 78 exits an aperture 82 formed in radiation shield 74.

Positioner 70 includes a source adapter arm 86 connected to radiation shield 74. Source adapter arm 86 is preferably attached to a flange member 88 provided with one or more roller elements 90 which slide along track 76, so that arm 86 moves together with radiation shield 74. The spatial position of arm 86 is thus determined by the position of radiation source 72. Radiation beam 78 is preferably collimated by a beam collimator 84 attached to arm 86 which defines a beam axis 85.

Preferably a source adapter arm positioning assembly 92 is provided for adjusting attachment of arm 86 with respect to radiation shield 74 and radiation source 72. Assembly 92 may be merely a plurality of adjustment screws or may include more elaborate adjustment equipment, such as a step motor or actuator. Assembly 92 may adjust the position of arm 86 relative to radiation source 72 along and/or about any axis, such as beam axis 85 or a curvilinear axis corresponding to the shape of track 76, for example.

A frame adapter arm 94 is pivotably attached to source adapter arm 86 about a pivot axis 96. Arm 94 defines a frame axis 98 intersecting pivot axis 96. Pivot axis 96 and frame axis 98 are selected such that when arm 86 is fixed relative to radiation source 72, pivot axis 96 and frame axis 98 both intersect radiation axis 80. Preferably pivot axis 96 and frame axis 98 both intersect radiation axis 80 generally at the same location, and most preferably substantially at the same location, designated by reference numeral 100. Pivot axis 96 and frame axis 98 are preferably generally orthogonal.

Arm 94 includes a distal portion 102 which is preferably attached to a patient support frame 104 such that frame 104 is rotatable about frame axis 98. As seen in FIG. 2, frame axis 98 is preferably the azimuth axis and pivot axis 96 is preferably the elevation axis.

There is preferably provided a table 108 upon which a patient (not shown) may be supported. The head of the patient is affixed to a head ring 110 of frame 104 such that location 100 lies in a target of the patient which is to be irradiated. Table 108 is rotatable about a table axis 112, as is well known in the art. Table axis 112 ideally generally coincides with frame axis 98. It is a particular feature of the present invention that even if table axis 112 is misaligned with frame axis 98, source adapter arm 86 always positions location 100 in a desired orientation with respect to radiation source 72 and frame adapter arm 94 always positions location 100 in a desired orientation with respect to patient support frame 104, i.e., radiation beam 78 substantially intersects location 100 and the target no matter how radiation shield 74, radiation source 72 or table 108 has moved or sagged. Radiation source 72 thus "drags" the target of the patient with it no matter where it goes or how it sags, and accurate irradiation of the target is ensured.

A frame adapter arm positioning assembly 114, such as an X-Y-Z positioner, is preferably pivotably mounted to frame adapter arm 94 and attached to patient support frame 104. Assembly 114 adjusts mounting of patient support frame 104 to arm 94. Assembly 114 moves patient support frame 104 along three mutually orthogonal axes (typically corresponding to axes 96 and 98 and to a longitudinal table axis 116, for example), so that the target can be properly aligned with location 100.

Figure 3:
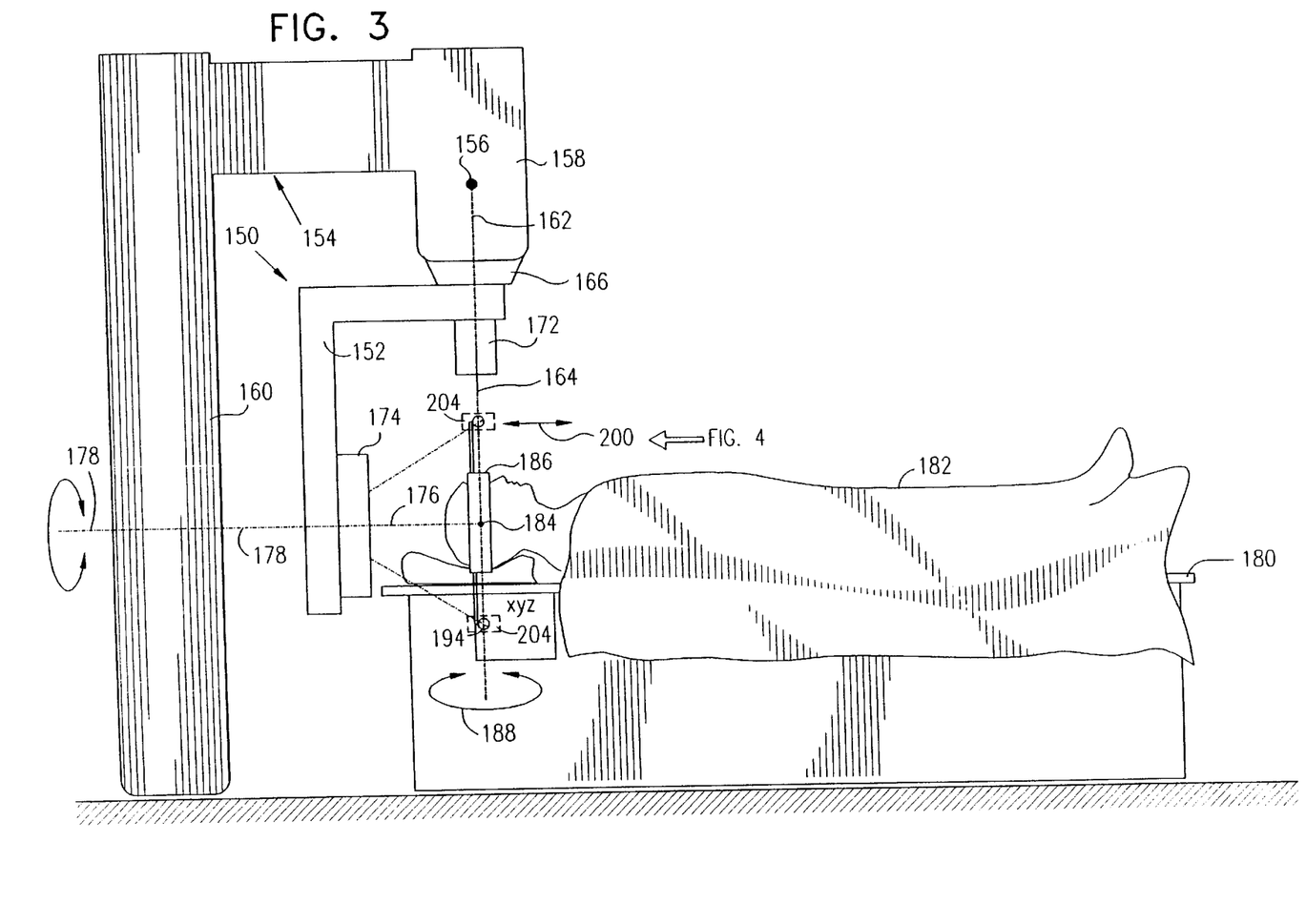
FIG. 3 is a simplified pictorial illustration of a positioner for stereotactic radiation treatment constructed and operative in accordance with yet another preferred embodiment of the present invention.

Reference is now made to FIG. 3 which illustrates a positioner 150 for stereotactic radiation treatment, constructed and operative in accordance with yet another preferred embodiment of the present invention.

Positioner 150 includes a source adapter arm 152 arranged to be attached to a housing 154 of a radiation source 156. For example, arm 152 may be suspended or at least partially suspended from a portion of a tray or turret 158 of a LINAC gantry 160. Radiation source 156 emits a radiation beam 162 along a beam axis 164. Preferably a source adapter arm positioning assembly 166 is provided for adjusting attachment of arm 152 to the radiation source 156. Assembly 166 may adjust the position of arm 152 relative to radiation source 156 along and/or about any of three mutually orthogonal axes, such as beam axis 164 and axes in a plane perpendicular to beam axis 164, for example. Assembly 166 may include any conventional step motor, actuator or the like, for adjusting the position of arm 152. A beam collimator 172 is preferably mounted onto arm 152 for collimating radiation beam 162. By virtue of the attachment of arm 152 to radiation source 156, the spatial position of arm 152 is determined by the position of radiation source 156.

A measurement assembly 174 is attached to source adapter arm 152 for making measurements with respect to a measurement axis 176. Assembly 174 is preferably pivotally attached to arm 152 so that assembly pivots about axis 176. Source adapter arm 152 is preferably telescopic so that measurement axis 176 of measurement assembly 174 may be positioned at any desired position. Gantry 160, comprising therein radiation source 156, is rotatable about a gantry axis 178, as is well known in the art. Arm 152 is preferably initially positioned so that gantry axis 178 substantially coincides with measurement axis 176. Ideally, radiation source 156 rotates about gantry axis 178 synchronously with rotation of arm 152 about measurement axis 176. However, if gantry axis 178 is misaligned with measurement axis 176, measurement assembly 174 measures the misalignment and provides accurate correction data so that the radiation beam 162 can still be accurately directed through the desired target, as will be described hereinbelow.

There is preferably provided a table 180 upon which a patient 182 may be supported. Patient 182 has a target 184 which is to be irradiated by radiation beam 162. In the illustrated example, the head of patient 182 is affixed to a patient support frame (head ring) 186. As described above, in stereotactic radiation treatment, it is required that radiation beam 162 pass as close as possible to the ideal isocenter, i.e., the theoretical intersection of a rotational axis 188 (azimuth axis) of table 180, and the rotational axis 178 (roll axis) of gantry 160.

Figure 4:
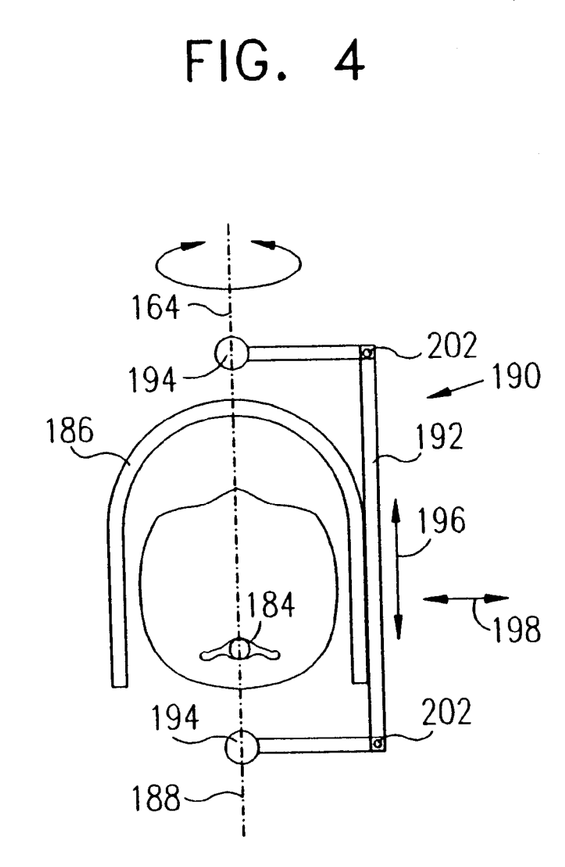
FIG. 4 is a simplified illustration of an optical target used with the positioner of FIG. 3, constructed and operative in accordance with a preferred embodiment of the present invention, wherein markers are initially aligned with a beam axis and azimuth axis of the positioner of FIG. 3.

Reference is now additionally made to FIG. 4 which illustrates a target assembly 190 constructed and operative in accordance with a preferred embodiment of the present invention. Target assembly 190 preferably includes a bar 192 from which extends at least one marker 194. Marker 194 may be a sphere or any other arbitrarily shaped marker which can be sensed easily and accurately by measurement assembly 174. Bar 192 is preferably slidingly attached to patient support frame 186 so that bar 192 can be adjusted along any of three mutually perpendicular axes 196, 198 (FIG. 4) and 200 (FIG. 3). Bar 192 is adjusted with respect to patient support frame 186 so that initially axes 188 and 164 substantially pass through a reference point (generally the center) of marker 194. Most preferably, two markers 194 are provided for redundancy, markers 194 being positioned so that they are substantially equidistant from target 184. Bar 192 may be either pre-bent or provided with joints 202 so that markers 194 may be accurately positioned with respect to axes 164 and 188 and target 184. Once the alignment of bar 192 and markers 194 with respect to target 184 has been achieved (and verified by any suitable technique), bar 192 is fixed to patient support frame 186 which is of course fixed relative to target 184.

Figure 5:
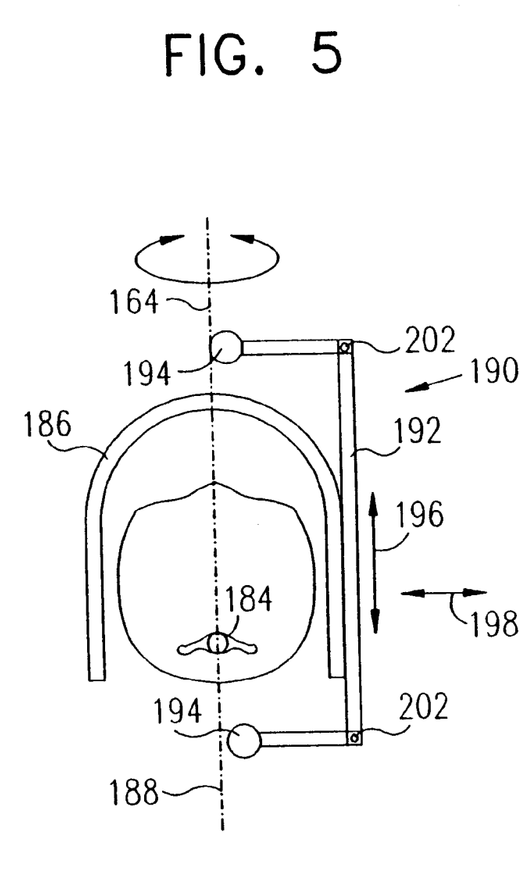
FIG. 5 is a simplified illustration of the optical target misaligned with the beam axis and azimuth axis of the positioner of FIG. 3.

As seen in FIGS. 3 and 4, markers 194 are initially substantially aligned with axes 164 and 188 and target 184 is substantially aligned at the isocenter, that is, the intersection of axes 176 (which is initially substantially the same as axis 178) and axis 164 (which is initially substantially aligned with axis 188). Upon rotation or any other movement of gantry 160 during radiotherapy, due to tolerances and other imperfections, target 184 may come out of alignment with the isocenter. However, markers 194 always remain at a constant, known predetermined spatial distance from target 184 because bar 192 and markers 194 have been fixed relative to target 184, as described above. Thus, any misalignment of target 184 relative to the isocenter is directly and exactly related to any misalignment of markers 194 from their ideal alignment with axes 164 and/or 188. An example of such a misalignment of markers 194 with respect to axes 164 and/or 188 is shown in FIG. 5.

Measurement assembly 174 measures the misalignment of markers 194. Most preferably, measurement assembly 174 comprises an optical measurement assembly, such as a type of theodolite which accurately measures angular changes (about axes 196, 198 and 200) in the position of markers 194. Since the initial distance of markers 194 from assembly 174 is known, the angular changes can be easily converted to distance changes as well. Alternatively, assembly 174 may comprise an optical range finder which measures the distance changes by means of laser reflections, as is well known in the art. Alternatively, assembly 174 need not be optical but can comprise non-optical measurement equipment as well, such as ultrasound, RF, or some kind of electromagnetic wave measurement equipment. Depending on the type of equipment used, markers 194 may be disposed in cylinders 204 which have an inner reflective surface. It is believed that such a reflective surface may be usefull in detecting changes in distance generally along axis 200.

Figure 6:
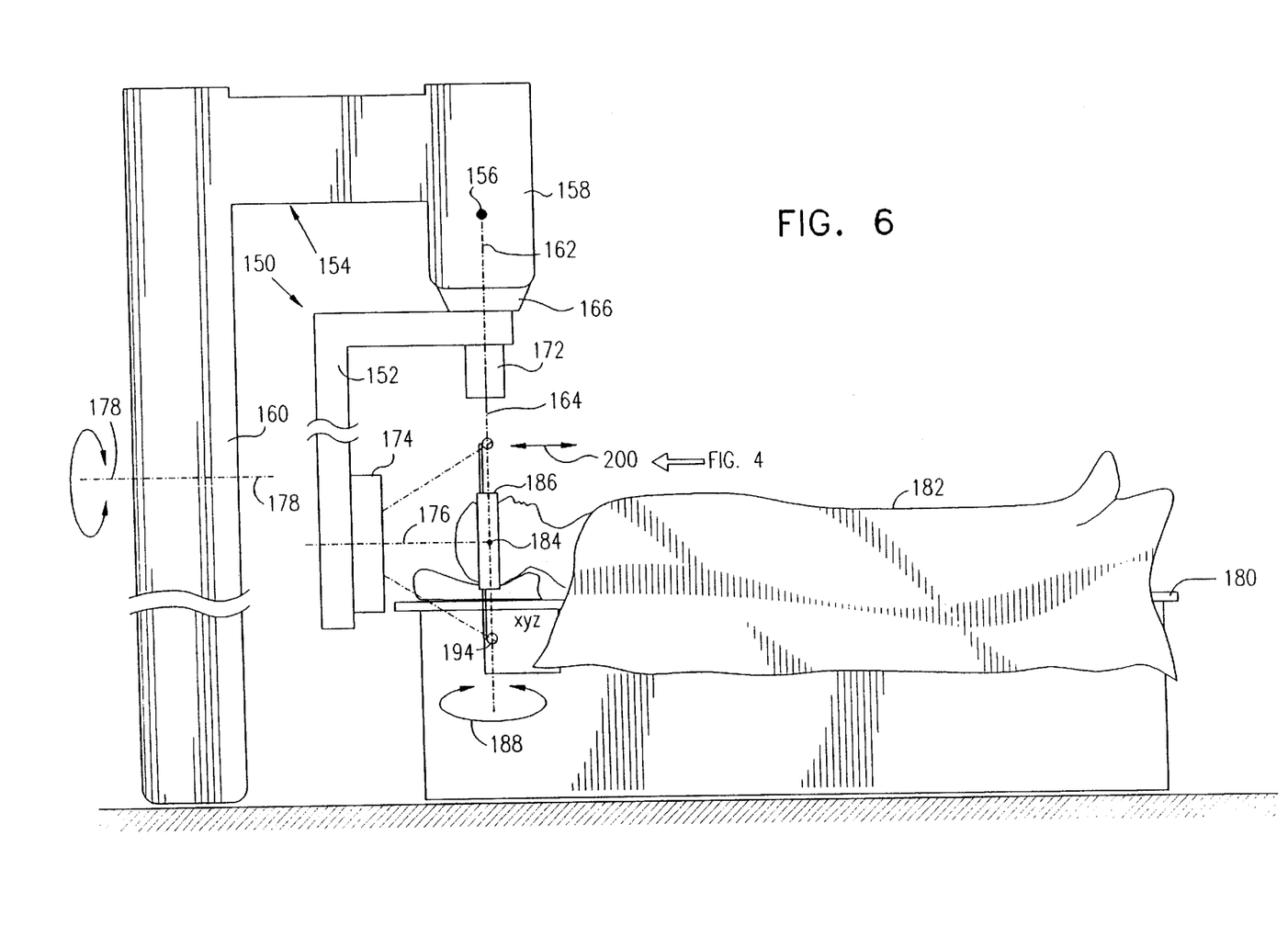
FIG. 6 is a simplified pictorial illustration of the positioner of FIG. 3 being used to perform stereotactic radiotherapy wherein a target to be irradiated is offset from the ideal isocenter, i.e., the theoretical intersection of a rotational axis (azimuth axis) of a table, and a rotational axis (roll axis) of a gantry.

Reference is now made to FIG. 6 which illustrates positioner 150 being used to perform stereotactic radiotherapy wherein the target 184 is offset from the ideal isocenter, i.e., the theoretical intersection of a rotational axis 188 (azimuth axis) of table 180, and the rotational axis 178 (roll axis) of gantry 160. By extending the telescopic arm 152, in effect a "new isocenter" is created, not at the intersection of axis 178 and 188 but rather at the intersection of measurement axis 176 of assembly 174 and azimuth axis 188. Thus, measurement axis 176 is offset generally parallel to rotational axis 178. In such an arrangement, it may be possible to carry out irradiation schemes which may not be possible with rotation about gantry axis 178. For example, in prior art systems, after a first radiation dose is administered, the gantry arm and/or table is moved in some discrete increment to another position for the next radiation dose. The entire radiotherapy consists of discrete incremental movements of the gantry and/or table with the radiation doses being delivered when the gantry and/or table has reached a stationary position. In the present invention, the offset position of the target relative to the rotation axis of the gantry arm may make possible delivery of radiation doses during continuous movement of the gantry and/or table.

Figure 7:
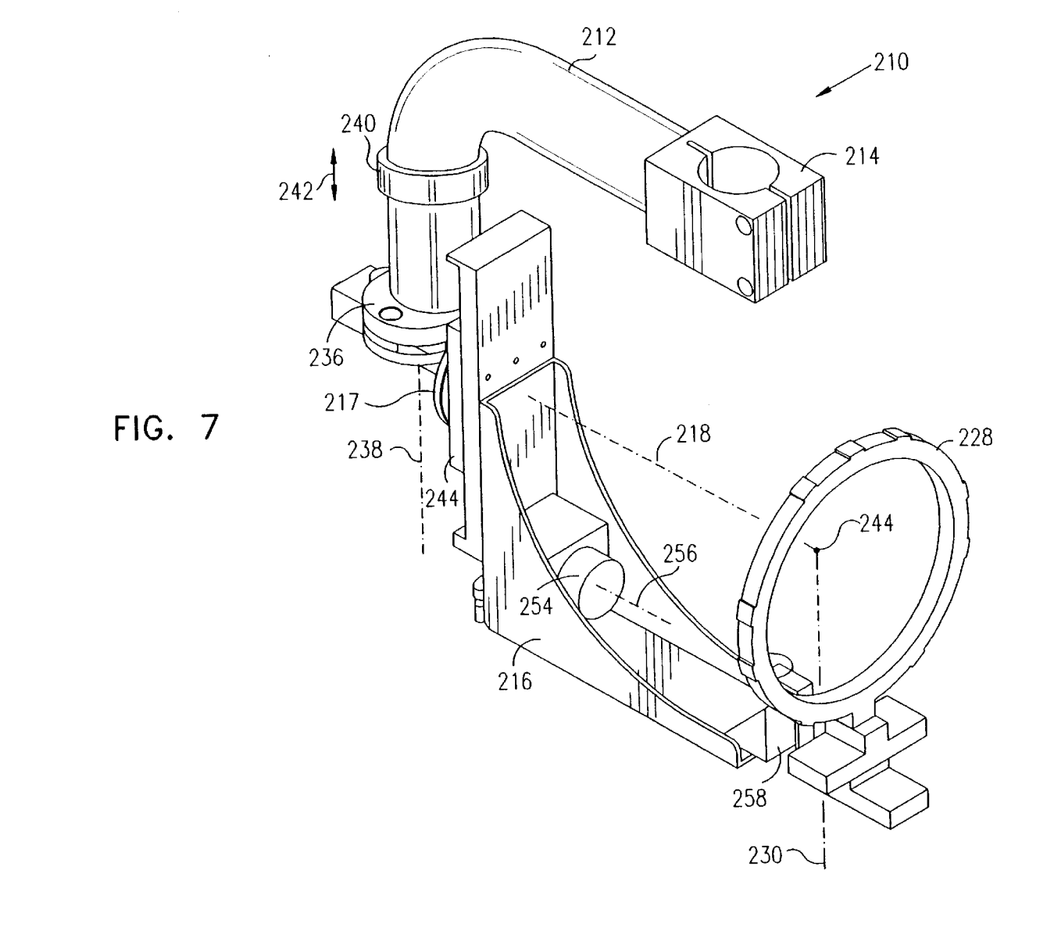
FIGS. 7 and 8 are simplified pictorial and side-view illustrations, respectively, of a positioner for stereotactic radiation treatment constructed and operative in accordance with still another preferred embodiment of the present invention.
Figure 8:
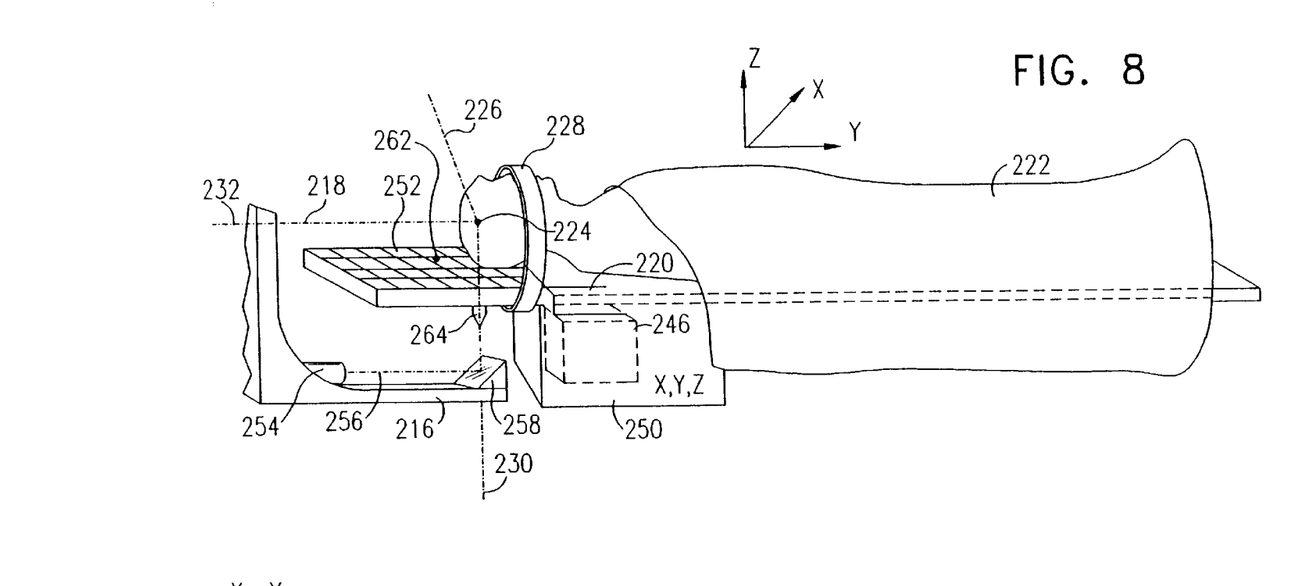

Reference is now made to FIGS. 7 and 8 which illustrate a positioner 210 for stereotactic radiation treatment, constructed and operative in accordance with still another preferred embodiment of the present invention. Positioner 210 preferably includes a source adapter arm 212 arranged to be attached to a housing of a radiation source, such as housing 14 or 154 of radiation source 16 or 156, as described hereinabove with reference to FIG. 1 or 3, respectively.

Source adapter arm 212 preferably includes a clamp block 214 for fixed attachment to a beam collimator, such as collimator 32 or 172, as described hereinabove with reference to FIG. 1 or 3, respectively. As with the embodiments described above, by virtue of the attachment of arm 212 to the radiation source, the spatial position of arm 212 is determined by the position of the radiation source.

Source adapter arm 212 is pivotably attached to a measurement assembly arm 216 at a bearing support 217 defining a measurement axis 218. Arm 212 is preferably initially positioned so that a gantry axis 232 (FIG. 8) substantially coincides with measurement axis 218. Ideally, the radiation source rotates about the gantry axis synchronously with rotation of source adapter arm 212 about measurement axis 218. However, if the gantry axis is misaligned with measurement axis 218, a measurement assembly is provided, as will be described hereinbelow, that measures the misalignment and provides accurate correction data so that the radiation beam can still be accurately directed through the desired target. In a typical use of positioner 210, measurement assembly arm 216 remains horizontal while the gantry arm and source adapter arm 212 rotate about axis 218. Of course, measurement assembly arm 216 translates (movement in X, Y, Z) together with the gantry arm and source adapter arm 212.

As seen in FIG. 8, there is preferably provided a table 220 upon which a patient 222 may be supported. Patient 222 has a target 224 which is to be irradiated by a radiation beam emanating along a beam axis 226. In the illustrated example, the head of patient 222 is affixed to a patient support frame (head ring) 228. As described above, in stereotactic radiation treatment, it is required that radiation beam axis 226 pass as close as possible to the ideal isocenter, i.e., the theoretical intersection of a rotational axis 230 (azimuth axis) of table 220, and rotational axis 232 (roll axis) of the gantry.

Measurement axis 218 and rotational axis 230 are selected such that when source adapter arm 212 is attached to the radiation source, measurement axis 218 and rotational axis 230 both intersect the beam axis 226. Preferably measurement axis 218 and rotational axis 230 both intersect beam axis 226 generally at the same location, and most preferably substantially at the same location, namely, at target 224.

Measurement axis 218 and rotational axis 230 are preferably generally orthogonal.

Preferably one or more positioning assemblies are provided for adjusting the linear and rotational orientations of source adapter arm 212 and measurement assembly arm 216 relative to each other. For example, source adapter arm 212 is preferably pivotally attached to measurement assembly arm 216 at another bearing support 236 defining an azimuth axis 238. An adjustment assembly 240 may be mounted on arm 212 for adjusting the length of arm 212 generally along axis 238, as indicated by a double arrow 242. After turning adjustment assembly 240 to adjust the length of arm 212, assembly 240 preferably fixes the position of arm 212 at the chosen adjustment point. Similarly, an adjustment assembly 244 may be mounted on measurement assembly arm 216 for adjusting the length of arm 216 generally along axis 238, again as indicated by double arrow 242. After sliding the adjustment assembly 244 to adjust the length of arm 216, assembly 244 preferably fixes the position of arm 216 at the chosen adjustment point.

As seen particularly in FIG. 8, patient support frame 228 is attached to a linear positioner 246, preferably an X-Y-Z table. Positioner 246 preferably provides fine adjustment of the position of frame 228 along the three mutually orthogonal axes X, Y and Z. Frame 228 and positioner 246 are preferably mounted to table 220 which is provided with an additional positioner 250. Positioner 250 preferably provides coarse adjustment of the position of frame 228 and positioner 246 along the three mutually orthogonal axes X, Y and Z. A coordinate board 252 is preferably fixedly mounted to frame 228. Coordinate board 252 may be, but is not necessarily, transparent.

An optical sensor, such as a camera 254, is preferably mounted on measurement assembly arm 216 and views coordinate board 252 via a mirror 258. Camera 254, mirror 258 and coordinate board 252 together comprise a measurement assembly that measures any misalignment of the ideal isocenter from the actual intersection of the table and gantry rotational axes 230 and 232, and provides accurate correction data to a motion controller so that the radiation beam can still be accurately directed through the desired target, as is now described with further reference to FIG. 9. (It is noted that alternatively coordinate board 252 may be mounted on measurement assembly arm 216 and camera 254 may be fixedly mounted on frame 228.)

Figure 9:
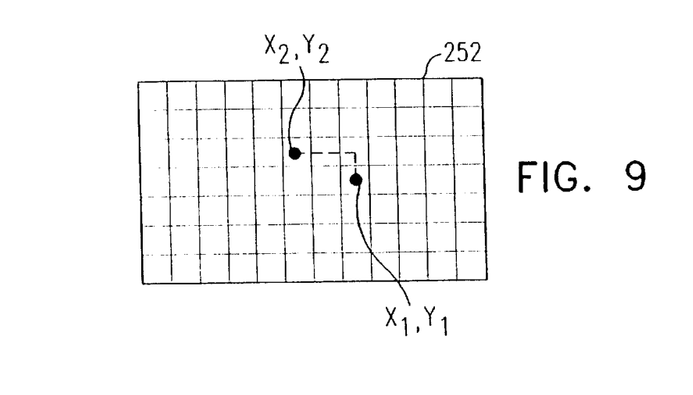
FIG. 9 is a simplified pictorial illustration of a coordinate board used with the positioner of FIGS. 7 and 8.

After initially aligning the intersection of measurement axis 218 (which itself is initially aligned with rotational axis 232 of the gantry, as mentioned above) and table rotational axis 230 at target 224, camera 254 views coordinate board 252 via mirror 258. As seen in FIG. 9, target 224 is initially projected on to the X-Y plane of coordinate board 252 at a point $(x_1,y_1)$. The point $(x_1,y_1)$ is viewed by camera 254, or alternatively may be sensed by a photosensor 262 built into pixels of coordinate board 252.

After rotating the gantry arm or the table, target 224 may become misaligned with the isocenter, as discussed hereinabove. For example, because of misalignment of target 224 in the x-y plane, target 224 may now be projected upon a new point $(x_2,y_2)$. The spatial differences in the x-y plane, namely $x_1-x_2$ and $y_1-y_2$, may then be fed, manually or automatically, to the motion control equipment of the radiotherapy system to correct for the misalignment and realign target 224 with the isocenter.

The z-coordinate of the target position in space may be provided by a pin 264 placed in coordinate board 252. Pin 264 protrudes through to the underside of board 252. The lower point 266, for example, of pin 264 may be used as the z-reference point, as is now explained with reference to FIG. 10 which illustrates the field of view of camera 254. It is seen that point 266 is initially at $z_1$. If the patient must be moved in the z-direction, i.e., raised or lowered, first measurement assembly arm 216 is raised or lowered, and then frame 228 is accordingly raised or lowered by means of positioner 246 or 250, until pin 264 returns to the initial point $z_1$.

Figure 10:
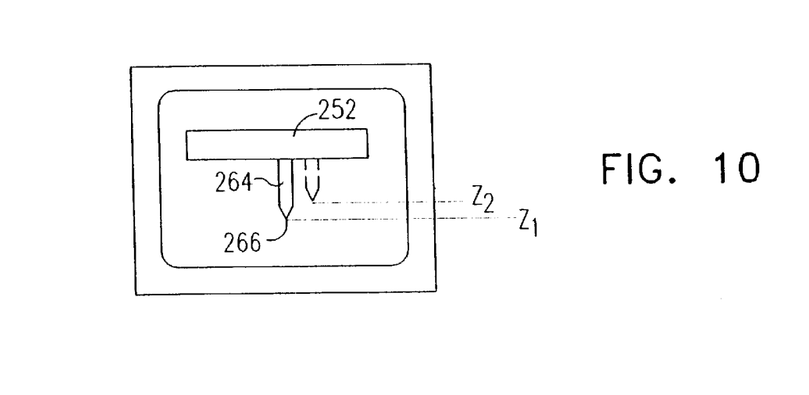
FIG. 10 is a simplified illustration of the field of view of an optical sensor used with the positioner of FIGS. 7 and 8.

After rotating the gantry arm or the table, target 224 may become misaligned with the isocenter, as discussed hereinabove, and point 266 may now be positioned at $z_2$. The spatial difference $z_1$–$z_2$ is sensed by camera 254 and may be fed to the motion control equipment of the radiotherapy system to correct for the misalignment and realign target 224 with the isocenter.

It is noted that measurement axis 218 may be offset generally parallel to gantry rotational axis 232, thereby defining a new isocenter at an intersection of measurement axis 218 and table rotational axis 230, as described hereinabove for the other embodiments of the present invention.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A positioner useful in stereotactic radiation treatment of a patient by radiation from a radiation source from which a radiation beam is emitted along a beam axis, the radiation source being housed in a housing attached to a gantry arm having a gantry rotational axis, the positioner comprising:
   a source adapter arm arranged to be attached to the radiation source such that the position of the source adapter arm is determined by the position of the radiation source, and the position of the source adapter arm relative to the radiation source is independent of the position of the gantry arm relative to the radiation source;
   a measurement assembly mounted on said source adapter arm for making measurements with respect to a measurement axis, said measurement axis initially substantially intersecting said beam axis, said measurement assembly measuring a misalignment of said measurement axis with said beam axis;
   a patient support frame having a frame axis; and
   a target assembly which comprises a bar slidingly attached to said patient support frame so that said bar is adjustable along any of three mutually perpendicular axes with respect to said frame, and wherein at least one marker extends from said bar, said marker being sensed by said measurement assembly and said marker being accurately positionable with respect to said beam axis, said measurement axis and said frame axis.

2. The positioner according to claim 1 wherein said patient support frame includes a frame axis about which a patient is rotatable, wherein the patient is rigidly mountable to said support frame such that a target of the patient is located at an intersection of said beam axis, said measurement axis and said frame axis.

3. The positioner according to claim 1 and further comprising a beam collimator mounted onto said source adapter arm for collimating said radiation beam.

4. The positioner according to claim 1 wherein said at least one marker always remains at a constant, known predetermined spatial distance from said target.

5. The positioner according to claim 1 wherein said bar is adjusted with respect to said patient support frame so that at least one of said beam axis and said frame axis substantially passes through a reference point of said marker.

6. The positioner according to claim 1 and further comprising two said markers which are positioned so that they are substantially equidistant from said target.

7. The positioner according to claim 1 wherein said measurement assembly measures angular position changes of said at least one marker relative to at least one of said beam axis, said measurement axis and said frame axis.

8. The positioner according to claim 1 wherein said measurement assembly measures linear position changes of said at least one marker relative to at least one of said beam axis, said measurement axis and said frame axis.

9. The positioner according to claim 1 wherein said measurement assembly comprises an optical measurement assembly.

10. A stereotactic radiation treatment system for treatment of a patient by radiation comprising:
   a radiation source from which a radiation beam is emitted along a beam axis, the radiation source being housed in a housing attached to a gantry arm having a gantry rotational axis;
   and a positioner comprising:
      a source adapter arm arranged to be attached to the radiation source such that the position of the source adapter arm is determined by the position of the radiation source, and the position of the source adapter arm relative to the radiation source is independent of the position of the gantry arm relative to the radiation source;
      a measurement assembly mounted on said source adapter arm for making measurements with respect to a measurement axis, said measurement axis initially substantially intersecting said beam axis, said measurement assembly measuring a misalignment of said measurement axis with said beam axis, wherein said measurement assembly comprises a coordinate board that has a fixed, known spatial relationship with an intersection of said beam axis and said measurement axis.

11. The stereotactic radiation treatment system according to claim 10 wherein said measurement axis is offset from said gantry axis.

12. A positioner useful in stereotactic radiation treatment of a patient by radiation from a radiation source from which a radiation beam is emitted along a beam axis, the radiation source being housed in a housing attached to a gantry arm having a gantry rotational axis, the positioner comprising:
   a source adapter arm arranged to be attached to the radiation source such that the position of the source adapter arm is determined by the position of the radiation source, and the position of the source adapter arm relative to the radiation source is independent of the position of the gantry arm relative to the radiation source;
   a measurement assembly mounted on said source adapter arm for making measurements with respect to a measurement axis, said measurement axis initially substantially intersecting said beam axis, said measurement assembly measuring a misalignment of said measurement axis with said beam axis, wherein said source adapter arm is telescopic.

13. A positioner useful in stereotactic radiation treatment of a patient by radiation from a radiation source from which a radiation beam is emitted along a beam axis, the radiation source being housed in a housing attached to a gantry arm having a gantry rotational axis, the positioner comprising:
- a source adapter arm arranged to be attached to the radiation source such that the position of the source adapter arm is determined by the position of the radiation source, and the position of the source adapter arm relative to the radiation source is independent of the position of the gantry arm relative to the radiation source;
- a measurement assembly mounted on said source adapter arm for making measurements with respect to a measurement axis, said measurement axis initially substantially intersecting said beam axis, said measurement assembly measuring a misalignment of said measurement axis with said beam axis, wherein said measurement assembly comprises a coordinate board that has a fixed, known spatial relationship with an intersection of said beam axis and said measurement axis.

14. A positioner useful in stereotactic radiation treatment of a patient by radiation from a radiation source from which a radiation beam is emitted along a beam axis, the radiation source being housed in a housing attached to a gantry arm having a gantry rotational axis, the positioner comprising:
- a source adapter arm arranged to be attached to the radiation source such that the position of the source adapter arm is determined by the position of the radiation source, and the position of the source adapter arm relative to the radiation source is independent of the position of the gantry arm relative to the radiation source;
- a measurement assembly mounted on said source adapter arm for making measurements with respect to a measurement axis, said measurement axis initially substantially intersecting said beam axis, said measurement assembly measuring a misalignment of said measurement axis with said beam axis;
- a patient support frame about which a patient is rotatable, wherein the patient is rigidly mountable to said support frame such that a target of the patient is located at an intersection of said beam axis, said measurement axis and a frame axis, wherein said measurement assembly comprises a coordinate board that has a fixed, known spatial relationship with an intersection of said beam axis, said measurement axis and said frame axis.

15. The positioner according to claim 13 and further comprising a pin protruding from a surface of said coordinate board, said pin having a point with a fixed, known spatial relationship with an intersection of said beam axis and said measurement axis.

16. The positioner according to claim 14 and further comprising a pin protruding from a surface of said coordinate board, said pin having a point with a fixed, known spatial relationship with an intersection of said beam axis, said measurement axis and said frame axis.

17. The positioner according to claim 14 wherein said measurement assembly comprises an optical sensor that measures any misalignment of said beam axis from at least one of said measurement axis and said frame axis.

18. The positioner according to claim 17 wherein said measurement assembly provides correction data based on said misaligmnent to a motion controller so that the radiation beam can be accurately directed through a desired target.

19. A positioner useful in stereotactic radiation treatment of a patient by radiation from a radiation source from which a radiation beam is emitted along a beam axis, the radiation source being housed in a housing attached to a gantry arm having a gantry rotational axis, the positioner comprising:
- a source adapter arm arranged to be attached to the radiation source such that the position of the source adapter aim is determined by the position of the radiation source, and the position of the source adapter arm relative to the radiation source is independent of the position of the gantry arm relative to the radiation source;
- a measurement assembly mounted on said source adapter arm for making measurements with respect to a measurement axis, said measurement axis initially substantially intersecting said beam axis, said measurement assembly measuring a misalignment of said measurement axis with said beam axis;
- a patient support frame about which a patient is rotatable, wherein the patient is rigidly mountable to said support frame such that a target of the patient is located at an intersection of said beam axis, said measurement axis and said frame axis,
- wherein said measurement axis is offset generally parallel to the gantry rotational axis, thereby defining a new isocenter at an intersection of said measurement axis and said frame axis.

* * * * *